United States Patent
Younis et al.

(10) Patent No.: US 12,097,232 B1
(45) Date of Patent: Sep. 24, 2024

(54) **METHOD OF PREVENTING CADMIUM-INDUCED RENAL TOXICITY USING A PLANT PRODUCT DERIVED FROM *ACHILLEA MILLEFOLIUM* L**

(71) Applicant: KING FAISAL UNIVERSITY, Al-Ahsa (SA)

(72) Inventors: Nancy Safwat Younis, Al-Ahsa (SA); Maged Elsayed Mohamed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/424,092

(22) Filed: Jan. 26, 2024

(51) Int. Cl.
  *A61K 36/28* (2006.01)
  *A61P 13/12* (2006.01)

(52) U.S. Cl.
  CPC .............. *A61K 36/28* (2013.01); *A61P 13/12* (2018.01); *A61K 2236/331* (2013.01)

(58) Field of Classification Search
  None
  See application file for complete search history.

(56) References Cited

U.S. PATENT DOCUMENTS

2008/0014291 A1   1/2008   Noack

FOREIGN PATENT DOCUMENTS

CN   112121072 A   12/2020

OTHER PUBLICATIONS

Jeyaprakash et al., "Effect of Spirulina and Liv.52 on Cadmium induced Toxicity in Albino Rats", Indian Journal of Experimental Biology (2005): 43 (September), 773-781.

Bafrani HH, et al. "Biochemical and Pathological Study of Hydroalcoholic Extract of *Achillea millefolium* L. on Ethylene Glycol-Induced Nephrolithiasis in Laboratory Rats". N Am J Med Sci. Dec. 2014;6(12):638-42. doi: 10.4103/1947-2714.147981. PMID: 25599052; PMCID: PMC4290053.

Begum et al. "Nephroprotective Effect of Aqueous Extract of Anisoon (*Pimpinella anisum*) and Brinjasif (*Achillea mellifolium/Artemesia vulgaris*) Management of Renal Failure in Experimental Animals Induced Paracetamol", Internation Journal of Pharmacy & Pharmaceutical Research, Mar. 2023 vol. 26, Issue:4.

*Primary Examiner* — Russell G Fiebig (74) *Attorney, Agent, or Firm* — Nath, Goldberg & Meyer; Joshua B. Goldberg

(57) ABSTRACT

A method of preventing cadmium-induced renal toxicity using a plant product derived from *Achillea millefolium* L. In an embodiment, the plant product is selected from an extract of *Achillea millefolium* L and an essential oil of *Achillea millefolium* L.

20 Claims, 4 Drawing Sheets
Specification includes a Sequence Listing.

SEQUENCE LISTING

```
Sequence total quantity: 8
SEQ ID NO: 1            moltype = DNA  length = 21
FEATURE                 Location/Qualifiers
source                  1..21
                        mol_type = other DNA
                        organism = synthetic construct
SEQUENCE: 1
aggctgacaa ggctcgttat g                                                 21

SEQ ID NO: 2            moltype = DNA  length = 20
FEATURE                 Location/Qualifiers
source                  1..20
                        mol_type = other DNA
                        organism = synthetic construct
SEQUENCE: 2
tgtcatccgc agcagtgttg                                                   20

SEQ ID NO: 3            moltype = DNA  length = 24
FEATURE                 Location/Qualifiers
source                  1..24
                        mol_type = other DNA
                        organism = synthetic construct
SEQUENCE: 3
catgacatcc cttattcaac caag                                              24

SEQ ID NO: 4            moltype = DNA  length = 21
FEATURE                 Location/Qualifiers
source                  1..21
                        mol_type = other DNA
                        organism = synthetic construct
SEQUENCE: 4
gccatgcctt gtcttcaatt g                                                 21

SEQ ID NO: 5            moltype = DNA  length = 21
FEATURE                 Location/Qualifiers
source                  1..21
                        mol_type = other DNA
                        organism = synthetic construct
SEQUENCE: 5
```

```
gccatgcctt gtcttcaatt g                                                            21

SEQ ID NO: 6           moltype = DNA  length = 20
FEATURE                Location/Qualifiers
source                 1..20
                       mol_type = other DNA
                       organism = synthetic construct
SEQUENCE: 6
ctgtttctgc tggttgcgta                                                              20

SEQ ID NO: 7           moltype = DNA  length = 26
FEATURE                Location/Qualifiers
source                 1..26
                       mol_type = other DNA
                       organism = synthetic construct
SEQUENCE: 7
atcatcaaca tgagaaacga tctgta                                                       26

SEQ ID NO: 8           moltype = DNA  length = 20
FEATURE                Location/Qualifiers
source                 1..20
                       mol_type = other DNA
                       organism = synthetic construct
SEQUENCE: 8
cagcggtcca gaagactcag                                                              20
```

METHOD OF PREVENTING CADMIUM-INDUCED RENAL TOXICITY USING A PLANT PRODUCT DERIVED FROM *ACHILLEA MILLEFOLIUM* L.

INCORPORATION BY REFERENCE OF MATERIAL SUBMITTED IN COMPUTER READABLE FORM

The Applicants hereby incorporate by reference the sequence listing contained in the ASCII text file titled 33160_41u_sequence.xml, created Jan. 12, 2024 and having 15 KB of data.

BACKGROUND

1. Field

The disclosure of the present patent application relates to preventing cadmium toxicity, and particularly, to preventing cadmium toxicity using a plant product derived from *Achillea millefolium* L.

2. Description of the Related Art

*Achillea millefolium*, commonly known as yarrow, is a flowering plant of the *Achillea* Asteraceae family. The plant is native to Asia, Europe, and North America. Several species have been employed as garden ornaments. Due to its antiphlogistic, spasmolytic, stomachic, carminative, and cholagogue properties, the plant has been used for medicinal purposes. While yarrow is most used in the treatment of gastrointestinal disorders, it is also utilized as a bitter aromatic, to increase bile output, and as an antioxidant.

In general, cadmium is used to manufacture nickel-cadmium rechargeable batteries, metal plating, and rods in nuclear reactors to control atomic fission reaction. Cadmium is a soft, malleable, ductile, and bluish white metal with respective atomic number, atomic mass, and electronic configuration viz. 48, 112.4, and [Kr] $4d^{10}5s^2$.

Cadmium-induced renal toxicity is associated with exposure to cadmium. Cadmium is absorbed in the blood primarily through ingestion or inhalation. Once absorbed, it accumulates in the kidneys, where it has a long half-life, leading to prolonged exposure. The kidneys are particularly vulnerable to cadmium toxicity because they are the primary route for its elimination from the body. Cadmium exerts its toxic effects on the kidneys through several mechanisms including proximal tubular damage, oxidative stress, and inflammation.

Thus, a method of preventing cadmium-induced renal toxicity solving the aforementioned problems are desired.

SUMMARY

The present subject matter relates to a method of preventing cadmium-induced renal toxicity in a subject or patient using a plant product derived from *Achillea millefolium* L. In an embodiment, the plant product is selected from an essential oil of *Achillea millefolium* L.

In other embodiments, the present subject matter relates to a method of preventing cadmium-induced renal toxicity in a subject or patient using a pharmaceutical composition comprising a plant product derived from *Achillea millefolium* L. and a pharmaceutically acceptable carrier.

These and other features of the present subject matter will become readily apparent upon further review of the following specification and drawings.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, the subject is eligible for treatment, e.g., treatment of cadmium-induced renal toxicity.

As used herein, the term "patient" refers to any single subject for which treatment is desired. In certain embodiments, the patient herein is a human. A subject can be considered to be in need of treatment.

An "effective amount" of a composition as described herein is an amount sufficient to carry out a specifically stated purpose. An "effective amount" may be determined empirically and in a routine manner, in relation to the stated purpose. The term "therapeutically effective amount" refers to an amount of a composition as described herein to "treat" a disease or disorder in a subject.

"Reducing", "reduce", or "reduction" means decreasing the severity, frequency, or length of one or more symptoms of a disease, disorder, or condition as described herein.

"Treating" or "treatment" or "alleviation" refers to both therapeutic treatment and prophylactic or preventative measures, wherein the object is to prevent or slow down (lessen) the targeted pathologic disease, condition, or disorder. Those in need of treatment include those already with the disease, condition, or disorder as well as those prone to have the disease, condition, or disorder or those in whom the disease, condition, or disorder is to be prevented. A subject or mammal is successfully "treated" for a disease, condition, or disorder if, after receiving a therapeutic amount of a composition as described herein, the subject shows observable and/or measurable reduction in, or absence of, one or more symptoms of the disease, condition, or disorder. Reduction of these signs or symptoms may also be felt by the patient.

The present subject matter relates to a method of preventing cadmium-induced kidney toxicity in a subject or patient, comprising administering an essential oil of *Achillea millefolium* L. (also identified herein as "AEO") to a subject in need thereof.

In one aspect, the present subject matter relates to a method of preventing cadmium-induced kidney toxicity in a subject or patient comprising administering an essential oil of *Achillea millefolium* L. to a subject in need thereof. In an embodiment, the essential oil of *Achillea millefolium* L. is prepared by drying a plant or plant part of *Achillea millefolium* L. to provide a dried sample; subjecting the dried sample to hydro-distillation to provide a volatile fraction; and recovering the volatile fraction to provide the essential oil. In one embodiment, the volatile fraction is recovered by decantation and dried over anhydrous sodium sulphate to provide the essential oil.

In another aspect, the present subject matter relates to a method of preventing cadmium-induced kidney toxicity in a subject or patient, comprising administering an essential oil of *Achillea millefolium* L. to a subject in need thereof. In one embodiment, the essential oil of *Achillea millefolium* L. can be obtained from a plant part selected from at least one of the leaf, root, and flower of *Achillea millefolium* L.

An embodiment of the present subject matter is directed to a pharmaceutical composition comprising an essential oil of *Achillea millefolium* L. and a pharmaceutically acceptable carrier.

An embodiment of the present subject matter is directed to a method of making a pharmaceutical composition including mixing the plant product of *Achillea millefolium* L. with a pharmaceutically acceptable carrier. For example, the method of making a pharmaceutical composition can include mixing the plant product of *Achillea millefolium* L. with a pharmaceutically acceptable carrier with preservatives, buffers, and/or propellants to create the pharmaceutical composition.

To prepare the pharmaceutical composition, the essential oil of *Achillea millefolium* L., as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The essential oil of *Achillea millefolium* L. can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the essential oil of *Achillea millefolium* L. or an amount effective to treat a disease, such as cadmium-induced kidney toxicity, may be determined initially from the examples described herein and adjusted for specific targeted diseases using routine methods.

The pharmaceutical composition can be administered to a subject in need thereof, particularly in a therapeutically effective amount, which applies to all treatment methods described herein. In an embodiment, the pharmaceutical composition can be administered to a subject in need thereof to treat cadmium-induced kidney toxicity.

The plant product of *Achillea millefolium* L. or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Preparation of Essential Oil of *Achillea millefolium* (AEO)

The dried whole plant of Yarrow (*Achillea millefolium* L., family Astraceae) was collected from local farms in Al-Ahsa, Eastern province, Kingdom of Saudi Arabia, in January 2022. The plant was kindly identified by taxonomist in Saudi Arabia and in Egypt.

The dried *A. millefolium* whole plants (100 g) were cut and subjected to hydro-distillation using Clevenger-type apparatus for 3 hours. The volatile fraction (yield; 0.85% v/dried weight) was recovered by decantation and dried over anhydrous sodium sulphate. The essential oil samples were kept in brown vials in the refrigerator at 4° C. until further use.

Example 2

Activity

Thirty-two adult male Wistar rats (8-9 weeks old, weighing, 160-180 g) were purchased from the Experimental Animal Research Centre, King Saud University, Riyadh, KSA.

All the animals were maintained with typical laboratory food and water ad libitum in a ventilated cage system (12 h light/dark cycle, 20.3-23.1° C.) throughout the whole experiment.

To study the renal protective activity of *Achillea millefolium* essential oil (AEO) on $CdCl_2$-induced renal toxicity, rats were randomly divided into four groups (n=8 per group). Control rats were orally administered saline 1 h before injected intraperitoneally (i.p.) with 0.9% NaCl (physiological saline) daily for 5 days. The $CdCl_2$ group was orally administered saline 1 h before injected i.p. with 6.5 mg/kg $CdCl_2$ daily for 5 days. The AEO group was orally administered AEO (200 mg/kg) 1 h before injected with 0.9% NaCl (physiological saline) daily for 5 days. The AEO+$CdCl_2$ group was orally administered AEO (100 mg/kg) 1 h before injected 6.5 mg/kg $CdCl_2$ i.p. daily for 5 days. $CdCl_2$ was dissolved in physiological saline. AEO was orally administered at a dose of 250 mg/kg, according to a preliminary study that showed no toxicity at this dose, whereas $CdCl_2$ was i.p. injected at 6.5 mg/kg as mentioned before.

Rats were euthanized (decapitation) 24 hours after the final dosing. The kidneys were dissected, weighed to obtain the weight and then divided into 2 parts. The $1^{st}$ part was homogenized in ice-cold 10 mM phosphate buffer (pH 7.4) to produce a 10% (w/v) homogenate for biochemical analysis. The $2^{nd}$ part was kept at −80° C. for quantitative real-time qRT-PCR.

The Cd concentrations in renal tissues were estimated as mentioned before. In brief, specimens of renal tissue were weighed and washed with 1 M nitric acid at 150° C. for 2 hours. The washed specimens were diluted with deionized water to 50 ml. The levels of metal were measured by atomic absorption spectrophotometry in a graphite furnace at 228.8 nm. The Cd values are expressed as microgram per gram of wet renal tissue.

Example 3

Determination of Kidney Function Biomarkers

Biomarkers of kidney function, i.e., Blood urea nitrogen (BUN), uric acid, and creatinine, were evaluated by using specific commercial kits. N-acetyl-β-D-glucosaminidase (NAG) is a marker of tubular toxicity was assessed using ELISA kit.

Gene expression for the TLR pathway, High-mobility group box 1 (HMBG1), Toll-Like Receptor 4 (TLR4), myeloid differentiation primary response gene 88 (MYD88), and Nuclear factor kappa B (NFκB) were quantified via real-time PCR (qPCR) consuming the primers' sequences, shown in Table 1, in agreement with the method described elsewhere. Briefly, RNA was isolated and purified using a Trizol reagent kit (Invitrogen, Carlsbad, CA, USA), then a reverse transcription polymerase chain reaction (RT-PCR) kit (TaKaRa, Kusatsu, Shiga, Japan) to reverse transcription reaction following the manufacturer's procedures. qPCR was applied using a SYBR ExScript RT-PCR kit, and quantification examinations were accomplished via an Opticon-2 Real-time PCR reactor (MJ Research, Capital Court, Reno, NV, USA). qPCR results were obtained using Step PE Applied Biosystems (Waltham, MA, USA) software. Relative gene expression data were calculated as mentioned earlier by the Livak and Schmittgen [5] method ($2^{-\Delta\Delta Cq2}$) and presented as a fold change. Target gene expressions were assessed and related to the reference gene (β-actin), and the results are shown in the figures as relative expression.

TABLE 1

Primer sequences used for qPCR of TLR pathway gene expression.

| Genes | Primer sequence (5' to 3') |
|---|---|
| HMGB-1 | 5'-AGGCTGACAAGGCTCGTTATG-3' (sense) (SEQ ID NO. 1)<br>5'-TGTCATCCGCAGCAGTGTTG-3' (antisense) (SEQ ID NO. 2) |
| TLR4 | 5'-CATGACATCCCTTATTCAACCAAG-3' (sense) (SEQ ID NO. 3)<br>5'-GCCATGCCTTGTCTTCAATTG-3' (antisense) (SEQ ID NO. 4) |
| MyD88 | 5'-GAGATCCGCGAGTTTGAGAC-3' (sense) (SEQ ID NO. 5)<br>5'-CTGTTTCTGCTGGTTGCGTA-3' (antisense) (SEQ ID NO. 6) |
| NFκB | 5'-ATCATCAACATGAGAAACGATCTGTA-3' (sense) (SEQ ID NO. 7)<br>5'-CAGCGGTCCAGAAGACTCAG-3' (antisense) (SEQ ID NO. 8) |
| Bax | 5'-GTGGTTGCCCTCTTCTACTT TG-3' (sense) (SEQ ID NO. 9)<br>3'-CACAAAGATGGTCACTGTCTGC-5' (antisense) (SEQ ID NO. 10) |

TABLE 1-continued

Primer sequences used for qPCR of TLR pathway gene expression.

| Genes | Primer sequence (5' to 3') |
|---|---|
| Bcl-2 | 5'-CCGGGAGATCGTGATGAAGT-3' (sense) (SEQ ID NO. 11)<br>3'-ATC CCAGCCTCCGTTATC CT-5' (antisense) (SEQ ID NO. 12) |
| β-Actin | 5'-TGCTATGTT GCCCTAGACTTCG-3' (sense) (SEQ ID NO. 13)<br>5'-GTTGGCATAGAG GTCTTTACGG-3' (antisense)(SEQ ID NO. 14) |

Lipid peroxidation was assessed according to the amount of malondialdehyde (MDA). The content of reduced glutathione (GSH) was evaluated and the activities of Catalase (CAT), Superoxide dismutase (SOD) and glutathione peroxidase (GPx) were estimated using kits.

Inflammation markers including interferon gamma (IFN-γ), monocyte chemoattractant protein-1 (MCP-1), tumor necrosis factor alpha (TNF-α), and interleukin 10 (IL-10) were measured using ELISA kits.

The actions of AEO administration on the apoptotic markers, such as caspase-3 and caspase 9 were evaluated.

Data were shown as mean±SD. Multiple comparisons was performed using one-way ANOVA followed by Tukey-Kramer as a post hoc test. The 0.05 level of probability was used as the significance level. Statistical analyses were executed using GraphPad software (version 8, San Diego, CA, USA).

Example 4

Determination of Kidney Function Biomarkers

Changes in Kidney Weight $CdCl_2$ administration resulted in a reduction in kidney weight. However, AEO administration significantly attenuated the adverse effects of $CdCl_2$ by restoring the changes in kidney weight (Table 2).

Changes in Cd Level in Renal Tissue $CdCl_2$ injection in rats significantly increased ($p<0.05$) the concentration of Cd in renal tissue when related to control group. The increased Cd concentration in the renal tissue was significantly ($p<0.05$) reduced by administration of AEO prior to $CdCl_2$-injection. See Table 2.

TABLE 2

Effect of AEO on kidney weight, renal Cd concentration and renal function tests in cadmium-administered rats

|  | Control | AEO | CdCl2 | AEO + CdCl2 |
|---|---|---|---|---|
| Kidney wt. (g) | 2.07 ± 0.15 | 2.01 ± 0.17 | 1.43 ± 0.11* | 1.91 ± 0.25 # |
| Cd concentration (μg/g renal tissue) | 0.036 ± 0.001 | 0.029 ± 0.003 | 0.95 ± 0.01 | 0.45 ± 0.02 |
| Creatinine (mg/dL) | 0.27 ± 0.02 | 0.21 ± 0.01 | 0.68 ± 0.01* | 0.38 ± 0.02# |
| BUN (mg/dL) | 15.25 ± 0.63 | 14.35 ± 0.21 | 40.66 ± 3.15* | 23.67 ± 2.21# |
| Uric acid (mg/dL) | 2.81 ± 0.22 | 2.97 ± 0.25 | 4.54 ± 0.15* | 3.4 ± 0.65 # |
| NAG (mIU/ml) | 8.9 ± 1.1 | 7.9 ± 1.5 | 33.2 ± 6.8 * | 13.2 ± 3.6 # |

All values are stated as mean ± SD.

*designates statistically significant compared to control group, and # designates statistically significant compared to $CdCl_2$ group, ($p < 0.05$) using one-way ANOVA followed by Tukey's post hoc test.

Changes in Renal Function Tests

Rats exposed to Cd-induced exhibited acute kidney injury, indicated by increases in the levels of serum creatinine, BUN and uric acid when compared to control group. Treatment with AEO significantly ameliorated these metabolite amplifications (Table 2).

Changes on Renal TLR41MYD88 NFκB Pathway Gene Expression

Figure 1A:
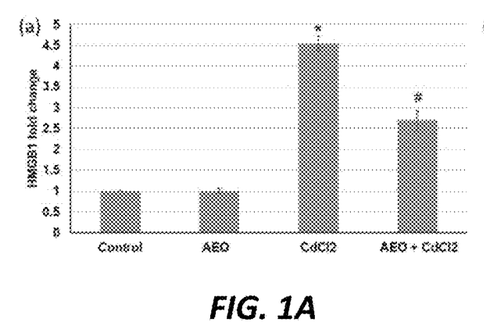
FIGS. 1A-1D are graphs showing effects of an essential oil of *Achillea millefolium* L. (AEO) administration on the gene expression of (1A) HMGB1, (1B) TLR4, (1C) MYD88, and (1D) NFκB in Cd-induced renal toxicity (all values are stated as mean±SD. * designates statistically significant compared to control group, and #designates statistically significant compared to $CdCl_2$ group, ($p<0.05$) using one-way ANOVA followed by Tukey's post hoc test).
Figure 1B:
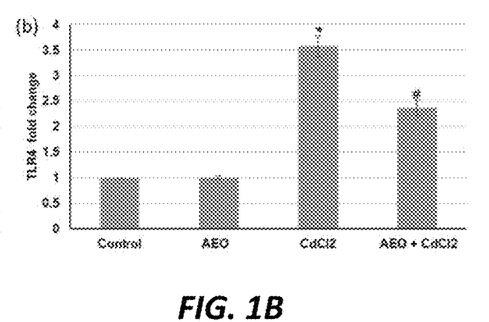
Figure 1C:
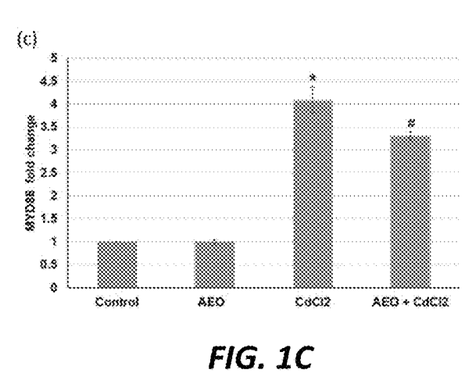
Figure 1D:
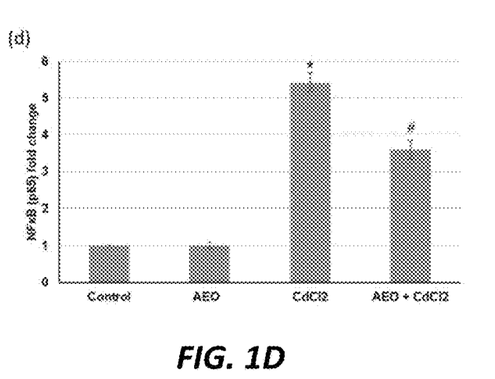

Injury caused by Cd produces several proteins such as HMGB1, which signal through TLRs, particularly TLR4, to trigger numerous inflammatory mediators including NFκB. Therefore, to examine the underlying mechanism of AEO on Cd induced renal toxicity, we tried to explore the mRNA expression levels of HMGB1, TLR4, and their adaptor protein MYD88 and finally NFκB to have an overview on the whole pathway. HMGB1 mRNA expression level was increased in Cd administered rats, whereas AEO lowered HMGB1 expression, (FIGS. 1A-1D). With HMGBlescalation, TLR4, and their adaptor protein MYD88 were amplified significantly in Cd experienced animals, while AEO administration significantly lowered mRNA expression of TLR4, and MYD88. Additionally, nuclear NFκB p65 was significantly augmented in the Cd group, whereas NFκB p65 level was substantially diminished in rats received AEO compared to the Cd group (FIGS. 1A-1D).

Figure 2A:
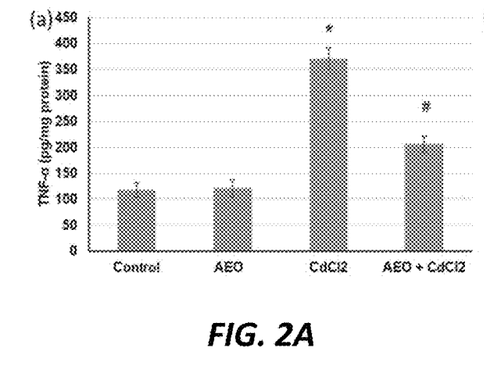
FIGS. 2A-2D are graphs showing effects of essential oil of *Achillea millefolium* L. (AEO) administration on the renal inflammatory mediators including (2A) TNF-α, (2B) IFN-γ, (2C) MCP-1, and (2D) IL-10 in Cd induced renal toxicity (all values are stated as mean±SD. * designates statistically significant compared to control group, and #designates statistically significant compared to $CdCl_2$ group, ($p<0.05$) using one-way ANOVA followed by Tukey's post hoc test).
Figure 2B:
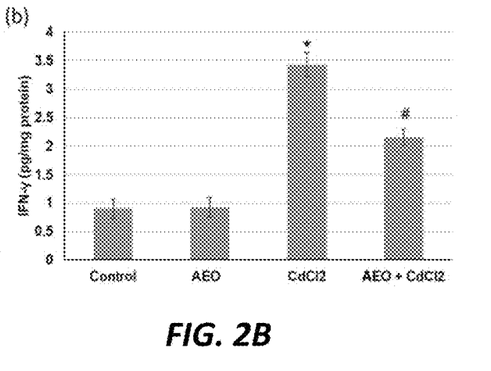
Figure 2C:
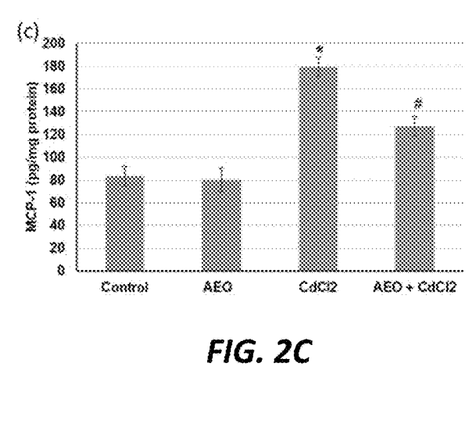
Figure 2D:
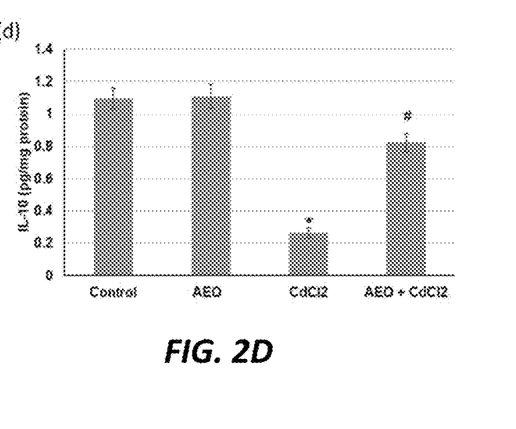

Inflammation was inspected via the detection of several cytokines and inflammatory mediators. TNF-α, IFN-7, and MCP-1 renal levels were amplified in the $CdCl_2$ group, whereas AEO administration distinctly prevented TNF-α, IFN-γ, and MCP-1 boost in $CdCl_2$. On the other hand, the level of IL-10, a cytokine that retains protective effects was declined following $CdCl_2$ administration, whereas AEO administration prohibited IL-10 reductions (FIGS. 2A-2D).

Changes in Renal Oxidative Stress

Figure 3A:
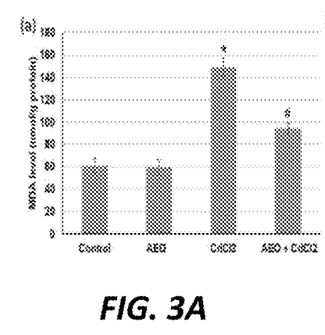
FIGS. 3A-3E are graphs showing effects of essential oil of *Achillea millefolium* L. (AEO) administration on the renal oxidative stress including (3A) MDA, (3B) SOD, (3C) CAT, (3D) GPx, and (3E) GSH in Cd induced renal toxicity (all values are stated as mean±SD. * designates statistically significant compared to control group, and #designates statistically significant compared to $CdCl_2$ group, ($p<0.05$) using one-way ANOVA followed by Tukey's post hoc test).
Figure 3B:
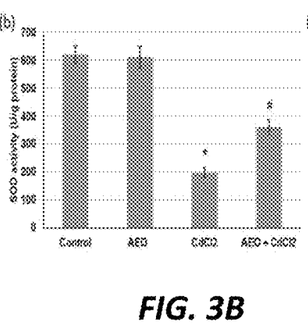
Figure 3C:
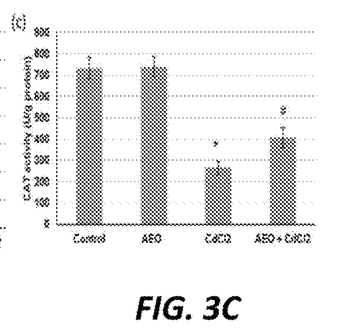
Figure 3D:
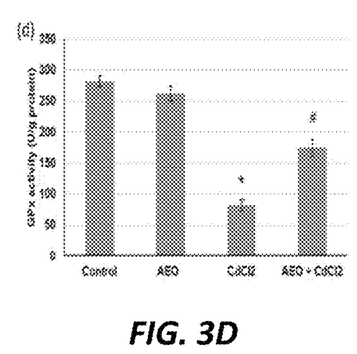
Figure 3E:
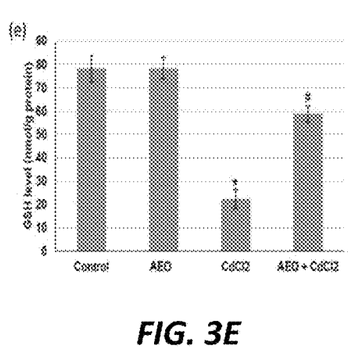

MDA levels were augmented in $CdCl_2$-experienced animals compared to the control, while AEO administration prevented the amplification in MDA level, indicating mitigated lipid peroxidation. Furthermore, the current invention verified that in $CdCl_2$ administered rats, the activities of SOD, CAT, and GPx were considerably declined, whereas AEO administration enhanced SOD, CAT, and GPx activities (FIGS. 3A-3E). Additionally, $CdCl_2$ caused an obvious reduction in renal GSH content related to the control group, whereas AEO markedly amplified GSH renal content.

Changes in Renal Apoptosis

Figure 4A:
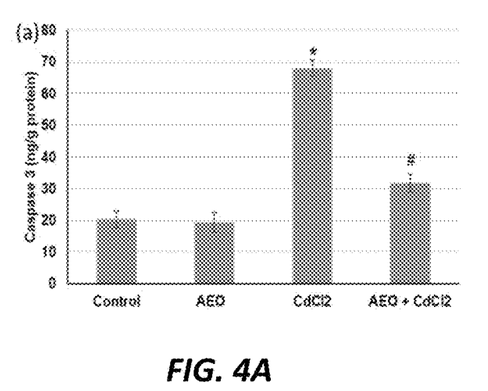
FIGS. 4A-4D are graphs showing effects of essential oil of *Achillea millefolium* L. (AEO) administration on the renal apoptosis markers including the level of (4A) Caspase 3 and (4B) Caspase 9, and the gene expression of (4C) Bax and (4D) Bcl2 in Cd induced renal toxicity (all values are stated as mean±SD. * designates statistically significant compared to control group, and #designates statistically significant compared to $CdCl_2$ group, ($p<0.05$) using one-way ANOVA followed by Tukey's post hoc test).
Figure 4B:
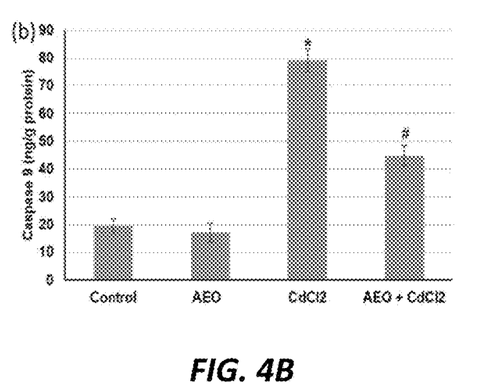
Figure 4C:
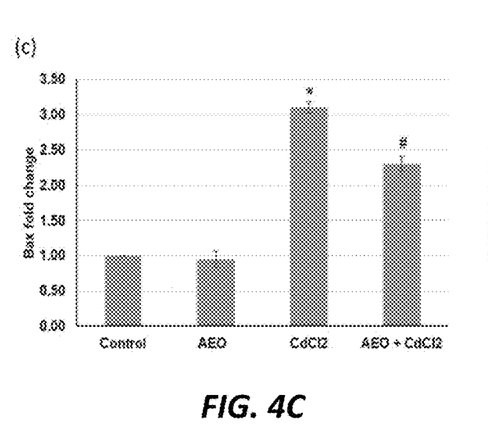
Figure 4D:
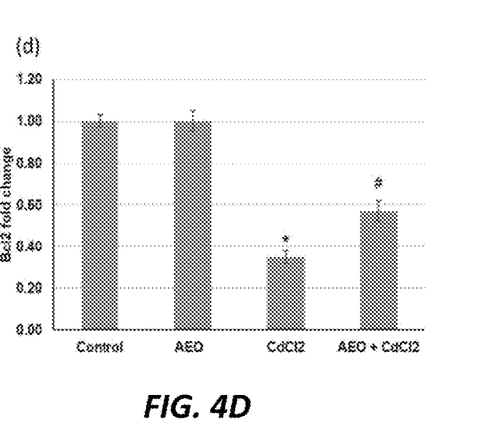

Caspase 3 and 9, as well as Bax gene expression, crucial members in apoptosis, were augmented subsequent to $CdCl_2$ renal injury, whereas $Bcl_2$ gene expression was diminished. On the other hand, AEO lessened caspase 3 and 9 renal contents and Bax gene expression and elevated $Bcl_2$. These results reflect the anti-apoptotic actions of AEO, which may be related to the alleviation of $CdCl_2$-induced renal toxicity (FIGS. 4A-4D).

It is to be understood that the method of preventing cadmium-induced kidney toxicity is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

---

We claim:

1. A method of protecting against cadmium-induced kidney toxicity in a patient, comprising:
   administering an essential oil of *Achillea millefolium* L. to a patient in need thereof.

2. The method of claim 1, wherein the essential oil of *Achillea millefolium* L. is obtained by a method comprising:
   drying a plant or plant part of *Achillea millefolium* L. to provide a dried sample;
   subjecting the dried sample to hydro-distillation to provide a volatile fraction; and
   recovering the volatile fraction to provide the essential oil.

3. The method of claim 2, wherein the plant part is selected from at least the leaf, root, and flower of *Achillea millefolium* L.

4. A method of protecting against pFeVe-ting-cadmium-induced kidney toxicity in a patient, comprising:
   administering a pharmaceutical composition comprising an essential oil of *Achillea millefolium* L. and a pharmaceutically acceptable carrier to a patient in need thereof.

5. The method of claim 4, wherein the essential oil of *Achillea millefolium* L. is obtained by a method comprising:
   drying a plant or plant part of *Achillea millefolium* L. to provide a dried sample; subjecting the dried sample to hydro-distillation to provide a volatile fraction; and recovering the volatile fraction to provide the essential oil.

6. The method of claim 5, wherein the plant part is selected from at least the leaf, root, and flower of *Achillea millefolium* L.

7. The method of claim 1, wherein the administration of the essential oil of *Achillea millefolium* L. decreases weight loss in the kidney of the patient after exposure to the cadmium as compared to a kidney not already treated with the essential oil of *Achillea millefolium* L.

8. The method of claim 1, wherein the administration of the essential oil of *Achillea millefolium* L. decreases a rise in cadmium concentration in the kidney of the patient after exposure to the cadmium as compared to a kidney not already treated with the essential oil of *Achillea millefolium* L.

9. The method of claim 1, wherein the administration of the essential oil of *Achillea millefolium* L. decreases a rise in creatine level in the kidney of the patient after exposure to the cadmium as compared to a kidney not already treated with the essential oil of *Achillea millefolium* L.

10. The method of claim 1, wherein the administration of the essential oil of *Achillea millefolium* L. decreases a rise in BUN level in the kidney of the patient after exposure to the cadmium as compared to a kidney not already treated with the essential oil of *Achillea millefolium* L.

11. The method of claim 1, wherein the administration of the essential oil of *Achillea millefolium* L. decreases a rise in uric acid level in the kidney of the patient after exposure to the cadmium as compared to a kidney not already treated with the essential oil of *Achillea millefolium* L.

12. The method of claim 1, wherein the administration of the essential oil of *Achillea millefolium* L. decreases a rise in NAG level in the kidney of the patient after exposure to the cadmium as compared to a kidney not already treated with the essential oil of *Achillea millefolium* L.

13. The method of claim 1, wherein the administration of the essential oil of *Achillea millefolium* L. lowers expression of TLR4 in the kidney of the patient after exposure to the cadmium as compared to a kidney not already treated with the essential oil of *Achillea millefolium* L.

14. The method of claim 1, wherein the administration of the essential oil of *Achillea millefolium* L. lowers MYD88 expression in the kidney of the patient after exposure to the cadmium as compared to a kidney not already treated with the essential oil of *Achillea millefolium* L.

15. The method of claim 1, wherein the administration of the essential oil of *Achillea millefolium* L. lowers NFκB p65 levels in the kidney of the patient after exposure to the cadmium as compared to a kidney not already treated with the essential oil of *Achillea millefolium* L.

16. The method of claim 1, wherein the administration of the essential oil of *Achillea millefolium* L. prevents an increase in TNF-α, IFN-γ, and MCP-1 renal levels in the kidney of the patient after exposure to the cadmium as compared to a kidney not already treated with the essential oil of *Achillea millefolium* L.

17. The method of claim 1, wherein the administration of the essential oil of *Achillea millefolium* L. prevents an amplification in MDA levels in the kidney of the patient after exposure to the cadmium as compared to a kidney not already treated with the essential oil of *Achillea millefolium* L.

18. The method of claim 1, wherein the administration of the essential oil of *Achillea millefolium* L. enhances SOD, CAT, and GPx activities in the kidney of the patient after exposure to the cadmium as compared to a kidney not already treated with the essential oil of *Achillea millefolium* L.

19. The method of claim 1, wherein the administration of the essential oil of *Achillea millefolium* L. lessens caspase 3 and 9 renal contents and Bax gene expression in the kidney of the patient after exposure to the cadmium as compared to a kidney not already treated with the essential oil of *Achillea millefolium* L.

20. The method of claim 1, wherein the administration of the essential oil of *Achillea millefolium* L. elevates Bcl2 levels in the kidney of the patient after exposure to the cadmium as compared to a kidney not already treated with the essential oil of *Achillea millefolium* L.

\* \* \* \* \*